United States Patent
Li et al.

(10) Patent No.: US 9,580,380 B2
(45) Date of Patent: Feb. 28, 2017

(54) METHOD FOR PREPARING DIAMINO-DICYCLOHEXYL METHANE

(71) Applicants: WANHUA CHEMICAL GROUP CO., LTD., Yantai, Shandong (CN); WANHUA CHEMICAL (NINGBO) CO., LTD., Ningo, Zhejiang (CN)

(72) Inventors: Xin Li, Shandong (CN); Hao Chen, Shandong (CN); Congying Zhang, Shandong (CN); Shan Gao, Shandong (CN); Zhenguo Liu, Shandong (CN); Weijia Wang, Shandong (CN); Lei Tang, Shandong (CN); Zhipeng Liu, Shandong (CN); Yuan Li, Shandong (CN); Qingmei Jiang, Shandong (CN); Jinhong Song, Shandong (CN); Weiqi Hua, Shandong (CN); Hao Ding, Shandong (CN)

(73) Assignee: Wanhua Chemical Group Co., Ltd., Ningbo, Zhejiang (CN)

( * ) Notice: Subject to any disclaimer, the term of this patent is extended or adjusted under 35 U.S.C. 154(b) by 0 days.

(21) Appl. No.: 14/761,890

(22) PCT Filed: Nov. 22, 2013

(86) PCT No.: PCT/CN2013/087661
§ 371 (c)(1),
(2) Date: Jul. 17, 2015

(87) PCT Pub. No.: WO2014/187094
PCT Pub. Date: Nov. 27, 2014

(65) Prior Publication Data
US 2016/0068472 A1     Mar. 10, 2016

(30) Foreign Application Priority Data

May 22, 2013    (CN) .......................... 2013 1 0190370

(51) Int. Cl.
*C07C 209/72*     (2006.01)
*B01J 38/08*      (2006.01)
*B01J 23/96*      (2006.01)

(52) U.S. Cl.
CPC ............. *C07C 209/72* (2013.01); *B01J 23/96* (2013.01); *B01J 38/08* (2013.01); *C07C 2101/14* (2013.01)

(58) Field of Classification Search
None
See application file for complete search history.

(56) References Cited

U.S. PATENT DOCUMENTS

| 5,196,594 A | 3/1993 | Schmelzer et al. |
| 2011/0251431 A1 | 10/2011 | Hoffmann et al. |

FOREIGN PATENT DOCUMENTS

| CN | 101429139 | 5/2009 |
| WO | 2004007425 | 1/2004 |

OTHER PUBLICATIONS

Wangshun et al. (English translation of CN 101429139).*
International Search Report (PCT/ISA/210) mailed on Feb. 27, 2014, by the Chinese Patent Office as the International Searching Authority for International Application No. PCT/CN2013/087661.

* cited by examiner

*Primary Examiner* — Sudhakar Katakam
*Assistant Examiner* — Jennifer C Sawyer
(74) *Attorney, Agent, or Firm* — Buchanan Ingersoll & Rooney

(57) ABSTRACT

Disclosed is a method for preparing diamino-dicyclohexyl methane ($H_{12}$MDA) by hydrogenation of diamino-diphenyl methane (MDA). In the process, 4,4'-MDA used as the starting material is firstly hydrogenated to prepare 4,4'-$H_{12}$MDA. When the activity of the catalyst is reduced, the feed is switched from 4,4'-MDA to the mixture of 2,4'-MDA and 4,4'-MDA, and then when the conversion is stabilized, the feed is switched to 4,4'-MDA again. The deactivated catalyst is activated on line by switching the feed to the mixture of 2,4'-MDA and 4,4'-MDA. 4,4'-$H_{12}$MDA having the trans-trans isomer content of 16~24 wt % is produced, and the mixture of 2,4'-$H_{12}$MDA and 4,4'-$H_{12}$MDA is also produced, wherein the content of 2,4'-$H_{12}$MDA in the mixture is 4~15 wt %.

19 Claims, No Drawings

METHOD FOR PREPARING DIAMINO-DICYCLOHEXYL METHANE

FIELD OF THE INVENTION

The present invention relates to a method for preparing diamino-dicyclohexyl methane by hydrogenation of diamino-diphenyl methane, particularly to a method for continuously preparing 4,4'-diamino-dicyclohexyl methane having the trans-trans isomer content of 16~24 wt %, in combination with the mixture of 2,4'-diamino-dicyclohexyl methane and 4,4'-diamino-dicyclohexyl methane wherein the content of 2,4'-diamino-dicyclohexyl methane is 4~15 wt %.

BACKGROUND OF THE INVENTION

Diamino-dicyclohexyl methane ($H_{12}$MDA) comprises isomers such as 4,4'-diamino-dicyclohexyl methane (4,4'-$H_{12}$MDA), 2,4'-diamino-dicyclohexyl methane (2,4'-$H_{12}$MDA), 2,2'-diamino-dicyclohexyl methane (2,2'-$H_{12}$MDA), etc. 4,4'-$H_{12}$MDA is primarily used for preparing a new generation of high performance anti-aging polyurethane dicyclohexyl methane diisocyanate ($H_{12}$MDI), which is suitable for preparing lightweight, stable performance of polyurethane coatings and paints. 4,4'-$H_{12}$MDA is also used as the amine component of the curing agent of epoxy resin and transparent nylon. 4,4'-$H_{12}$MDA comprises three types, i.e., trans-trans-, trans-cis-, cis-cis-, of isomers, referred simply to as trans-trans-isomer, trans-cis-isomer, cis-cis-isomer correspondingly.

Diamino-diphenyl methane (MDA) comprises isomers such as 4,4'-diamino-diphenyl methane (4,4'-MDA), 2,4'-diamino-diphenyl methane (2,4'-MDA), 2,2'-diamino-diphenyl methane (2,2'-MDA), etc. 4,4'-MDA is very difficult to be hydrogenated due to the stability and the steric hindrance of the aromatic ring. In most of the patents relating to catalytic hydrogenation of 4,4'-MDA, the catalytic reaction is conducted intermittently in a stirred tank reactor or fixed bed reactor at high temperature and high pressure by using a supported noble metal catalyst, in order to obtain a satisfactory yield and a suitable proportion of the trans-trans-isomer.

EP0231788 disclosed an improved batch hydrogenation process of 4,4'-MDA, which prepares 4,4'-$H_{12}$MDA having the trans-trans-isomer content of 17-24 wt % by using THF solvent and two component catalyst of rhodium and ruthenium at 170-195° C. and 700-1500 psig. Said patent did not provide a technical solution for restoring the catalytic activity by treating the catalyst using a certain technical means when the performance of the catalyst is reduced due to long time use.

The continuous production of 4,4'-$H_{12}$MDA is also mentioned in patent literatures. US20020198409 disclosed a process for the continuous reduction of 4,4'-MDA, wherein a powdered supported ruthenium catalyst having ruthenium metal content of 1-10% and powder micropore diameter of 5-150 μm is used to catalyze the reaction at the conditions of 130-200° C. and 50-400 bar in the reaction system having water content of less than 1% and alcohols used as the solvent in a series of suspension reactors consisting of continuous bubble columns. When the catalyst activity is decreased, it need to shut down the reaction system to clean the catalyst, which results in rise of the costs and is unfavourable for continuous production.

U.S. Pat. No. 5,196,594 disclosed a process for reducing 4,4'-MDA or the mixture of 2,4'-MDA, 2,2'-MDA and 4,4'-MDA by continuous hydrogenation, which prepares 4,4'-$H_{12}$MDA having the trans-trans isomer content of 18.5-23.5 wt % by using a supported ruthenium as the catalyst at 100-190° C. and 50-350 bar in at least one fixed bed reactor, wherein the support has BET specific area of about 70-280 $m^2$/g and average pore diameter of 10-320 Å. After 360 h of run, the yield of $H_{12}$MDA can still reach 93.7%, but the amount of the feed per hour processed by the catalyst is only 0.04-0.1 Kg MDA/Kg Cat, and it did not mention the method of regenerating the catalyst after deactivation of the catalyst.

In the continuous production of 4,4'-HMDA, the catalytic activity, selectivity and the like are reduced after long term run of the catalyst. The above-said patents did not mention the real-time regeneration of the catalyst during the continuous reaction. U.S. Pat. No. 3,071,551 disclosed a process of regenerating a rhodium catalyst by heating, but the process needs to discharge the catalyst and increase corresponding equipments to achieve the purpose, and thus it is very difficult to implement the process whether for batch mode or continuous mode. U.S. Pat. No. 3,856,862 disclosed a process for regenerating catalyst by a separate regenerating system, wherein the catalyst is regenerated by heating at high temperature in the presence of oxygen used as oxidizing agent in a special tubular reactor. Similarly, the technical solution needs to discharge the catalyst and to provide a special equipment to achieve regeneration of the catalyst.

There are the following drawbacks in the prior art:
1) The catalyst productivity is low, and the amount of the feed processed per hour by the catalyst is only 0.04-0.1 Kg MDA/Kg Cat.
2) When the activity of the catalyst is decreased, it needs to shut down the production system, and a separate equipment is required to regenerate the catalyst, which increases the investment costs and is unfavorable for continuous production.

SUMMARY OF THE INVENTION

The present invention is to provide a method for preparing 4,4'-$H_{12}$MDA by the hydrogenation of MDA, which regenerates the catalyst deactivated in the reaction of preparing 4,4'-$H_{12}$MDA from the hydrogenation of 4,4'-MDA, and recycles it for preparing 4,4'-$H_{12}$MDA. It can regenerate the catalyst on line without shutdown of the production system and rising of the reaction temperature and can also produce the mixture of 4,4'-$H_{12}$MDA and 2,4'-$H_{12}$MDA, and thus it can save the cost without reducing productivity.

The technical solution of the present invention used to achieve the above-said object is described as below.

The present invention provides a method for preparing $H_{12}$MDA, comprising the following steps:
1) 4,4'-MDA feed is hydrogenated in a reactor packed with catalyst to prepare 4,4'-$H_{12}$MDA at the conversion of 98-99.99%;
2) When the conversion in step 1) is 90-98%, preferably 95-98%, more preferably 96-98% (i.e., the conversion is decreased to 90-98%, preferably 95-98%, more preferably 96-98%), the feed is switched from 4,4'-MDA to a mixture of 2,4'-MDA and 4,4'-MDA, and the hydrogenation reaction is continued to prepare 2,4'-$H_{12}$MDA and 4,4'-$H_{12}$MDA;
3) After the conversion of the mixture of 2,4'-MDA and 4,4'-MDA in step 2) is ≥90% and the reaction is lasted at said conversion for 20-40 h, the feed is switched from the mixture of 2,4'-MDA and 4,4'-MDA to 4,4'-MDA, and the hydrogenation reaction is continued to prepare 4,4'-$H_{12}$MDA.

In the step 1) described in the present invention, the mean residence time of the feed is 30-90 min, the productivity of the catalyst is 0.4-1 g MDA/g cat/min, and the yield of $H_{12}MDA$ is 85-95%, wherein the trans-trans-isomer is 16-24 wt % based on the weight of 4,4'-$H_{12}MDA$.

In the step 2) described in the present invention, the mean residence time of the mixture of 2,4'-MDA and 4,4'-MDA is 30-90 min, the productivity of the catalyst is 0.4-1 g MDA/g cat/min, the conversion of the mixture of 2,4'-MDA and 4,4'-MDA is ≥90%, and the yield of $H_{12}MDA$ is 50-80%, wherein the trans-trans isomer is 16-24 wt % based on the weight of 4,4'-$H_{12}MDA$.

After switching the feed in the step 3) described in the present invention, the conversion is 98-99.99%, the yield of $H_{12}MDA$ is 85-95%, wherein the trans-trans-isomer is 16-24 wt % based on the weight of 4,4'-$H_{12}MDA$.

The conversion described in the present invention=
(the mass of MDA in the reactants–the mass of MDA in the reaction product)/(the mass of MDA in the reactants)×100%

The yield of $H_{12}MDA$ described in the present invention=(the mole number of $H_{12}MDA$ in the reaction product)/(the mole number of MDA in the reactants)×100%

The catalyst used in the step 1) described in the present invention is a supported metal catalyst, wherein the metal is one or more selected from Group VIIIB metals, preferably one or more selected from Pt, Rh, Ru, Ir and Pd, the support is one or more selected from rare earth, diatomaceous earth, alumina, activated carbon, lithium aluminate, spinel, titania, silica and silica-alumina oxides, and the weight ratio of the metal and the support is 1-10:100.

The catalyst described in the present invention is preferably a mixture of $Rh/Al_2O_3$ and $Ru/Al_2O_3$, wherein the weight ratio of Rh/Ru is 1-50:1, preferably 30-40:1, the content of Rh is 1-10 wt %, preferably 3-7 wt %, more preferably 4-6 wt %, based on the weight of $Rh/Al_2O_3$; and the content of Ru is 1-10 wt %, preferably 3-7 wt %, more preferably 4-6 wt %, based on the weight of $Ru/Al_2O_3$.

The reactor described in the present invention is a single reaction tank or multiple reaction tanks or fixed beds in series, preferably a single reaction tank or multiple reaction tanks in series. When a single reaction tank or multiple reaction tanks in series are used, the productivity of the catalyst for 4,4'-MDA in the step 1) described in the present invention is 0.4-1 g MDA/g cat/min, and the productivity of the catalyst for the mixture of 2,4'-MDA and 4,4'-MDA in the step 2) described in the present invention is 0.4-1 g MDA/g cat/min. The amount of $Rh/Al_2O_3$ in the reaction tank is 0.5-5 wt %, preferably 1-3 wt %, based on the total weight of the reaction solution in the reaction tank.

When the fixed beds are used, the space velocity of 4,4'-MDA feed in the step 1) described in the present invention is 0.4-1 g MDA/g cat/min, the space velocity of the mixture of 2,4'-MDA and 4,4'-MDA in the step 2) described in the present invention is 0.4-1 g MDA/g cat/min.

In the steps 1) and 3) described in the present invention, the 4,4'-MDA feed is composed of 98-100 wt % 4,4'-MDA, 0-2 wt % 2,4'-MDA, 0-1 wt % N-methyl-4,4'-diamino diphenyl methane (N—$CH_3$-4,4'-MDA), and 0-1 wt % other impurities, based on the total weight of the 4,4'-MDA feed; preferably of 99-100 wt % 4,4'-MDA, 0-1 wt % 2,4'-MDA, 0-0.5 wt % N—$CH_3$-4,4'-MDA, and 0-0.5 wt % other impurities, based on the total weight of the 4,4'-MDA feed.

In the step 2) described in the present invention, the mixture of 2,4'-MDA and 4,4'-MDA is composed of 83-95 wt % 4,4'-MDA, 3-16 wt % 2,4'-MDA, 0-1 wt % N—$CH_3$-4,4'-MDA, and 0-1 wt % other impurities, based on the total weight of the mixture; preferably of 85-95 wt % 4,4'-MDA, 5-15 wt % 2,4'-MDA, 0-0.5 wt % N—$CH_3$-4,4'-MDA, and 0-0.5 wt % other impurities, based on the total weight of the mixture.

The reaction temperature of hydrogenation in the steps 1), 2), 3) described in the present invention is 100-190° C., preferably 160-180° C.; and the absolute reaction pressure is 5-15 MPa, preferably 6-10 MPa.

The 4,4'-MDA feed in the steps 1) and 3) described in the present invention can be supplied in the absence of a solvent, but is preferably mixed with a solvent to form a solution feed, the concentration of 4,4'-MDA in the solution is 40-60 wt %, preferably 50 wt %.

The mixture of 2,4'-MDA and 4,4'-MDA in the step 2) described in the present invention can be supplied in the absence of a solvent, but is preferably mixed with a solvent to form a solution feed, the total concentration of 2,4'-MDA and 4,4'-MDA in the solution is 40-60 wt %, preferably 50 wt %.

The solvent described in the present invention comprises one or more selected from cyclohexane, dioxane, tetrahydrofuran, cyclohexylamine, dicyclohexylamine, methanol, ethanol, isopropanol, n-butanol, 2-butanol and methyl cyclohexane, preferably tetrahydrofuran (THF).

When the catalyst activity is decreased in the step 3) of the present invention, the regeneration step 2) of the catalyst may be repeated until the catalyst fails to restore its activity by the regeneration step 2) and to meet the requirements of production. Then the deactivated catalyst can be activated by using the existing technology in the art, such as the methods disclosed in U.S. Pat. No. 3,071,551, U.S. Pat. No. 3,856,862, and the reactivated catalyst can further be used for hydrogenation of MDA to prepare $H_{12}MDA$.

Since the catalytic system is a gas-liquid-solid three-phase reaction system, hydrogen needs to be transferred through a good mass transfer from the gas phase onto the surface of the catalyst to form an active hydrogen and then contacted with a reactive substrate on the catalyst surface, and thus the active hydrogen on the surface is consumed to achieve hydrogenation reaction. The hydrogenation productivity per unit of the catalyst is limited. When the feed rate exceeds the productivity of the catalyst, with the continuous addition of the feed, the consumption rate of the active hydrogen atoms on the catalyst surface is greater than the formation rate of them, and thus the catalyst is under the condition of hydrogen deficiency, which eventually leads to the continuous decrease of the catalytic activity. Due to the steric hindrance effect of 2,4'-MDA, its hydrogenation activity is significantly lower than that of 4,4'-MDA. When the long-term introduction of 4,4'-MDA leads to deactivation of the catalyst, by switching to the feed containing 2,4'-MDA, the speed of the hydrogenation reaction can be lowered, such that the formation rate of the active hydrogen atoms on the catalyst surface is greater than the consumption rate of them, which makes the activity of the catalyst restored. Compared with the catalyst regeneration in the traditional continuous preparation process of $H_{12}MDA$, the present invention may regenerate the constantly deactivated catalyst on-line during the continuous reaction by switching the composition of the feed, which may reduce the equipment investment cost, and may produce 2,4'-$H_{12}MDA$ continuously and thus improve the catalytic efficiency of the catalyst notably.

The positive effects of the present invention are as follows:

1. The productivity of the catalyst in the present invention is as high as 0.4-1 g MDA/g cat/min. When 4,4'-MDA is used as the feed, the conversion is 98-99.99% and the yield of $H_{12}$MDA is 85-95% wherein the trans-trans-isomer is 16-24 wt % based on the weight of 4,4'-$H_{12}$MDA; and when the mixture of 2,4'-MDA and 4,4'-MDA is used as the feed, the conversion of the mixture is 90%, the yield of $H_{12}$MDA is 50-80% wherein the trans-trans isomer is 16-24 wt % based on the weight of 4,4'-$H_{12}$MDA.

2. The present invention provides a method for continuously preparing 4,4'-$H_{12}$MDA having the trans-trans isomer content of 16~24 wt %, in combination with the mixture of 2,4'-$H_{12}$MDA and 4,4'-$H_{12}$MDA wherein the content of 2,4'-$H_{12}$MDA is 4~15 wt %, which notably promotes the catalytic efficiency of the catalyst.

3. The catalyst deactivated from the long-term run may be regenerated on-line, which simplifies the process design and saves the cost of the production.

THE MODE OF CARRYING OUT THE INVENTION

The present invention is further described with reference to the Examples, but should not be interpreted to be limited to these Examples.

Both 4 wt % Rh/$Al_2O_3$ and 5 wt % Ru/$Al_2O_3$ are available from Johnson Matthey Plc.
The starting material 4,4'-MDA is Wanamine MDA-100 from WANHUA Chemical Group Co., Ltd.
The MDA mixture containing 15 wt % 2,4'-MDA is available from WANHUA Chemical Group Co., Ltd.
The MDA mixtures containing 10 wt % and 5 wt % 2,4'-MDA are respectively prepared by mixing the above-said MDA mixture containing 15 wt % 2,4'-MDA with Wanamine MDA-100.

The main composition of the starting materials is as shown in table 1.

TABLE 1

| | The main composition of the starting materials | | | |
|---|---|---|---|---|
| starting materials | 4,4'- MDA/wt % | 2,4'- MDA/wt % | N—$CH_3$-4,4'- MDA/wt % | Other components/wt % |
| 4,4'-MDA | 99.5 | — | 0.35 | 0.15 |
| MDA mixture containing 5 wt % 2,4'-MDA | 94.5 | 5 | 0.36 | 0.14 |
| MDA mixture containing 10 wt % 2,4'-MDA | 89.5 | 10 | 0.35 | 0.15 |

TABLE 1-continued

| | The main composition of the starting materials | | | |
|---|---|---|---|---|
| starting materials | 4,4'- MDA/wt % | 2,4'- MDA/wt % | N—$CH_3$-4,4'- MDA/wt % | Other components/wt % |
| MDA mixture containing 15 wt % 2,4'-MDA | 84.5 | 15 | 0.35 | 0.15 |

The gas chromatograph is Agilent 6980 series manufactured by Agilent Technologies, DB capillary column, FID detector temperature: 300° C., the initial column temperature: 160° C., heated to 300° C. at 10° C./min, the retention time: 20 min.

Example 1

Into a 2 L volume autoclave are added 10 g of Rh(4 wt %)/$Al_2O_3$ catalyst and 0.2 g of Ru(5 wt %)/$Al_2O_3$ catalyst, along with 700 g of THF. At room temperature, the interior of the autoclave is replaced with 10 bar (absolute pressure) of $N_2$ and $H_2$ for three times respectively, and further pressurized to 45-50 bar (absolute pressure) by using $H_2$. At 180° C. and 8 MPa (absolute pressure), both the feed rate and discharge rate are 10 g/min, and firstly a THF solution of 4,4'-MDA (THF is 50 wt % based on the total weight of the solution) is fed. During the experiment, timing sampling is done and the samples are analyzed by gas chromatography, and the results are shown as in table 2.

As shown in table 2, when the conversion of MDA is reduced to 96.66%, the feed is switched from the THF solution of 4,4'-MDA to a THF solution of the MDA mixture containing 5 wt % 2,4'-MDA (THF is 50 wt % based on the total weight of the solution); and after the MDA conversion of the mixture maintains at 93-95% for 20 h, the feed is switched from the mixture to the THF solution of 4,4'-MDA (THF is 50 wt % based on the total weight of the solution). When the conversion of MDA is reduced to 96.73%, the feed is switched from the THF solution of 4,4'-MDA to the THF solution of the MDA mixture containing 5 wt % 2,4'-MDA (THF is 50 wt % based on the total weight of the solution). After the MDA conversion of the mixture maintains at 93-94% for 20 h, the feed is switched from the mixture to the THF solution of 4,4'-MDA (THF is 50 wt % based on the total weight of the solution). By switching to the solution of the MDA mixture containing 5 wt % 2,4'-MDA for two times, the catalyst still maintains high activity after 180 h, and when the feed is then switched to 4,4'-MDA, the conversion is still above 98%, and the yield of $H_{12}$MDA is above 85%.

TABLE 2

| | continuous reaction results of Example 1 | | | | |
|---|---|---|---|---|---|
| Reaction time (h) | MDA conversion (%) | $H_{12}$MDA yield (%) | 2,4'-$H_{12}$MDA/$H_{12}$MDA (%) | Content of tans-trans isomer based on 4,4'-$H_{12}$MDA [% (wt)] | Yield of high boiling components (%) |
| Feed: THF solution of 4,4'-MDA | | | | | |
| 10 | 97.12 | 84.34 | — | 18.55 | 3.12 |
| 20 | 98.94 | 90.12 | — | 19.04 | 5.37 |
| 30 | 99.11 | 90.78 | — | 18.92 | 5.31 |

TABLE 2-continued continuous reaction results of Example 1

| Reaction time (h) | MDA conversion (%) | H$_{12}$MDA yield (%) | 2,4'-H$_{12}$MDA/H$_{12}$MDA (%) | Content of tans-trans isomer based on 4,4'-H$_{12}$MDA [% (wt)] | Yield of high boiling components (%) |
|---|---|---|---|---|---|
| 40 | 99.02 | 90.24 | — | 19.17 | 5.81 |
| 50 | 96.66 | 81.43 | — | 18.12 | 5.12 |
| Feed is switched to THF solution of MDA mixture containing 5 wt % 2,4'-MDA ||||||
| 60 | 93.93 | 73.6 | 4.23 | 19.57 | 5.78 |
| 70 | 94.85 | 74.57 | 4.18 | 20.13 | 5.98 |
| 80 | 94.91 | 74.05 | 4.25 | 20.45 | 6.23 |
| Feed is switched to THF solution of 4,4'-MDA ||||||
| 90 | 98.41 | 86.17 | — | 19.24 | 8.15 |
| 100 | 98.45 | 86.45 | — | 19.84 | 8.38 |
| 110 | 98.42 | 86.29 | — | 19.56 | 8.46 |
| 120 | 96.73 | 79.32 | — | 19.04 | 8.57 |
| Feed is switched to THF solution of MDA mixture containing 5 wt % 2,4'-MDA ||||||
| 130 | 93.74 | 72.89 | 4.21 | 20.35 | 8.37 |
| 150 | 93.62 | 72.89 | 4.34 | 20.48 | 8.26 |
| Feed is switched to THF solution of 4,4'-MDA ||||||
| 160 | 98.33 | 85.89 | — | 19.22 | 8.57 |
| 180 | 98.41 | 85.67 | — | 19.38 | 8.66 |

Example 2

Into a 2 L volume autoclave are added 5 g of Rh(4 wt %)/Al$_2$O$_3$ catalyst and 0.13 g of Ru(5 wt %)/Al$_2$O$_3$ catalyst, along with 600 g of THF. At room temperature, the interior of the autoclave is replaced with 10 bar (absolute pressure) of N$_2$ and H$_2$ for three times respectively, and further pressurized to 80-85 bar (absolute pressure) by using H$_2$. At 170° C. and 12 MPa (absolute pressure), both the feed rate and discharge rate are 10 g/min, and firstly a THF solution of 4,4'-MDA (THF is 50 wt % based on the total weight of the solution) is fed. During the experiment, timing sampling is done and the samples are analyzed by gas chromatography, and the results are shown as in table 3.

As shown in table 3, when the conversion of MDA is reduced to 96.21%, the feed is switched from the THF solution of 4,4'-MDA to a THF solution of the MDA mixture containing 10 wt % 2,4'-MDA (THF is 50 wt % based on the total weight of the solution); and after the MDA conversion of the mixture maintains at 93-95% for 30 h, the feed is switched from the mixture to the THF solution of 4,4'-MDA (THF is 50 wt % based on the total weight of the solution). When the conversion of MDA is reduced to 96.11%, the feed is switched from the THF solution of 4,4'-MDA to the THF solution of the MDA mixture containing 10 wt % 2,4'-MDA (THF is 50 wt % based on the total weight of the solution). After the MDA conversion of the mixture maintains at 93-94% for 20 h, the feed is switched from the mixture to the THF solution of 4,4'-MDA (THF is 50 wt % based on the total weight of the solution). By switching to the solution of the MDA mixture containing 10 wt % 2,4'-MDA for two times, the catalyst still maintains high activity after 240 h, and when the feed is then switched to 4,4'-MDA, the conversion of MDA is above 98%, and the yield of H$_{12}$MDA is above 85%. After 260 h, the conversion of MDA is still up to 98.45%, but the yield of the high boiling components is increased to 8.57% due to lowering of the catalyst selectivity.

TABLE 3 continuous reaction results of Example 2

| Reaction time (h) | MDA conversion (%) | H$_{12}$MDA yield (%) | 2,4'-H$_{12}$MDA/H$_{12}$MDA (%) | Content of tans-trans isomer based on 4,4'-H$_{12}$MDA [% (wt)] | Yield of high boiling components (%) |
|---|---|---|---|---|---|
| Feed: THF solution of 4,4'-MDA ||||||
| 10 | 98.78 | 90.05 | — | 18.35 | 3.08 |
| 20 | 98.50 | 90.28 | — | 18.62 | 5.26 |
| 40 | 99.01 | 90.62 | — | 18.77 | 5.15 |
| 60 | 98.75 | 90.32 | — | 19.05 | 5.62 |
| 80 | 96.21 | 82.93 | — | 18.07 | 5.79 |
| Feed is switched to THF solution of MDA mixture containing 10 wt % 2,4'-MDA ||||||
| 90 | 93.93 | 72.02 | 8.73 | 20.23 | 5.25 |
| 100 | 93.85 | 71.87 | 8.60 | 21.01 | 5.52 |
| 120 | 94.11 | 71.52 | 8.72 | 20.65 | 5.13 |

TABLE 3-continued continuous reaction results of Example 2

| Reaction time (h) | MDA conversion (%) | $H_{12}$MDA yield (%) | 2,4'-$H_{12}$MDA/$H_{12}$MDA (%) | Content of tans-trans isomer based on 4,4'-$H_{12}$MDA [% (wt)] | Yield of high boiling components (%) |
|---|---|---|---|---|---|
| Feed is switched to THF solution of 4,4'-MDA | | | | | |
| 130 | 98.27 | 85.57 | — | 19.32 | 8.01 |
| 150 | 98.18 | 85.34 | — | 19.75 | 8.23 |
| 170 | 98.32 | 86.07 | — | 19.49 | 8.28 |
| 190 | 96.11 | 78.21 | — | 19.02 | 8.49 |
| Feed is switched to THF solution of MDA mixture containing 10 wt % 2,4'-MDA | | | | | |
| 200 | 93.34 | 71.08 | 8.58 | 20.56 | 8.22 |
| 220 | 93.02 | 70.32 | 8.60 | 20.69 | 8.15 |
| Feed is switched to THF solution of 4,4'-MDA | | | | | |
| 240 | 98.31 | 85.35 | — | 20.81 | 8.41 |
| 260 | 98.45 | 84.17 | — | 20.92 | 8.57 |

Example 3

Into a 2 L volume autoclave are added 15 g of Rh(4 wt %)/$Al_2O_3$ catalyst and 1 g of Ru(5 wt %)/$Al_2O_3$ catalyst, along with 500 g of THF. At room temperature, the interior of the autoclave is replaced with 10 bar (absolute pressure) of $N_2$ and $H_2$ for three times respectively, and further pressurized to 70-75 bar (absolute pressure) by using $H_2$. At 180° C. and 10 MPa (absolute pressure), both the feed rate and discharge rate are 15 g/min, and firstly a THF solution of 4,4'-MDA (THF is 50 wt % based on the total weight of the solution) is fed. During the experiment, timing sampling is done and the samples are analyzed by gas chromatography, and the results are shown as in table 4.

As shown in table 4, when the conversion of MDA is reduced to 96.95%, the feed is switched from the THF solution of 4,4'-MDA to a THF solution of the MDA mixture containing 15 wt % 2,4'-MDA (THF is 50 wt % based on the total weight of the solution); and after the MDA conversion of the mixture maintains at 91-92% for 20 h, the feed is switched from the mixture to the THF solution of 4,4'-MDA (THF is 50 wt % based on the total weight of the solution). When the conversion of MDA is reduced to 96.14%, the feed is switched from 4,4'-MDA to the THF solution of the MDA mixture containing 15 wt % 2,4'-MDA (THF is 50 wt % based on the total weight of the solution). After the MDA conversion of the mixture maintains at 91-92% for 20 h, the feed is switched from the mixture to the THF solution of 4,4'-MDA (THF is 50 wt % based on the total weight of the solution). By switching to the solution of the MDA mixture containing 15 wt % 2,4'-MDA for two times, after 160 h of reaction time and when the feed is switched to 4,4'-MDA, the conversion of MDA still reaches 98.07%, but the yield of the high boiling components is increased to 8.92% due to lowering of the catalyst selectivity, and thus the yield of $H_{12}$MDA is decreased to 84.62%.

TABLE 4 continuous reaction results of Example 3

| Reaction time (h) | MDA conversion (%) | $H_{12}$MDA yield (%) | 2,4'-$H_{12}$MDA/$H_{12}$MDA (%) | Content of tans-trans isomer based on 4,4'-$H_{12}$MDA [% (wt)] | Yield of high boiling components (%) |
|---|---|---|---|---|---|
| Feed: THF solution of 4,4'-MDA | | | | | |
| 10 | 97.57 | 85.35 | — | 18.63 | 3.26 |
| 20 | 99.16 | 90.45 | — | 18.94 | 5.16 |
| 30 | 99.23 | 90.34 | — | 18.59 | 5.81 |
| 40 | 99.18 | 90.03 | — | 19.01 | 6.05 |
| 50 | 96.95 | 80.82 | — | 18.07 | 5.68 |
| Feed is switched to THF solution of MDA mixture containing 15 wt % 2,4'-MDA | | | | | |
| 60 | 91.72 | 67.36 | 12.23 | 21.76 | 5.63 |
| 70 | 91.64 | 68.24 | 12.40 | 21.13 | 5.54 |
| 80 | 91.75 | 68.58 | 12.64 | 21.45 | 5.23 |
| Feed is switched to THF solution of 4,4'-MDA | | | | | |
| 90 | 98.11 | 86.47 | — | 19.89 | 8.56 |
| 100 | 98.47 | 85.52 | — | 19.62 | 9.12 |
| 110 | 98.35 | 85.87 | — | 19.48 | 8.42 |
| 120 | 96.14 | 77.58 | — | 19.26 | 8.52 |

TABLE 4-continued continuous reaction results of Example 3

| Reaction time (h) | MDA conversion (%) | $H_{12}$MDA yield (%) | 2,4'-$H_{12}$MDA/$H_{12}$MDA (%) | Content of tans-trans isomer based on 4,4'-$H_{12}$MDA [% (wt)] | Yield of high boiling components (%) |
|---|---|---|---|---|---|
| Feed is switched to THF solution of MDA mixture containing 15 wt % 2,4'-MDA | | | | | |
| 130 | 91.61 | 65.38 | 12.42 | 21.51 | 8.58 |
| 150 | 91.58 | 65.02 | 12.41 | 21.48 | 8.81 |
| Feed is switched to THF solution of 4,4'-MDA | | | | | |
| 160 | 98.07 | 84.62 | — | 19.76 | 8.92 |
| 180 | 98.15 | 84.57 | — | 19.58 | 9.09 |

Comparative Example 1

Into a 2 L volume autoclave are added 10 g of Rh(4 wt %)/$Al_2O_3$ catalyst and 0.2 g of Ru(5 wt %)/$Al_2O_3$ catalyst, along with 700 g of tetrahydrofuran (THF). At room temperature, the interior of the autoclave is replaced with 10 bar (absolute pressure) of $N_2$ and $H_2$ for three times respectively, and further pressurized to 45-50 bar (absolute pressure) by using $H_2$. At 180° C. and 8 MPa (absolute pressure), a THF solution of 4,4'-MDA (THF is 50 wt % based on the total weight of the solution) is fed at the feed rate of 10 g/min, and the reaction product is discharged at 10 g/min by a discharging pump. During the experiment, timing sampling is done and the samples are analyzed by gas chromatography, and the results are shown as in table 5.

TABLE 5 continuous reaction results of Comparative Example 1

| Reaction time (h) | MDA conversion (%) | $H_{12}$MDA yield (%) | Content of tans-trans isomer based on 4,4'-$H_{12}$MDA [% (wt)] | Yield of high boiling components (%) |
|---|---|---|---|---|
| 10 | 97.26 | 85.29 | 18.78 | 3.32 |
| 15 | 98.84 | 89.01 | 18.84 | 4.37 |
| 20 | 99.14 | 90.78 | 18.92 | 5.34 |
| 25 | 99.02 | 91.22 | 19.17 | 5.31 |
| 30 | 98.66 | 90.35 | 18.52 | 5.58 |
| 35 | 99.02 | 90.18 | 18.79 | 5.55 |
| 40 | 99.16 | 91.16 | 19.06 | 5.21 |
| 45 | 97.48 | 85.83 | 18.29 | 5.12 |
| 50 | 96.24 | 80.27 | 18.38 | 5.17 |
| 55 | 94.24 | 65.34 | 16.16 | 3.65 |
| 60 | 85.33 | 48.33 | 15.34 | 3.23 |
| 65 | 76.35 | 30.82 | 15.18 | 3.17 |

As shown in table 5, after the reaction time reaches 45 h, the activity of the catalyst is reduced, and as the reaction continues, the conversion of MDA and the yield of $H_{12}$MDA are further reduced, and the catalyst is deactivated significantly.

The invention claimed is:

1. A continuous method for preparing diamino-dicyclohexyl methane, wherein said continuous method comprises the following steps:
    1) 4,4'-diamino-diphenyl methane feed is hydrogenated in a reactor packed with catalyst to prepare 4,4'-diamino-dicyclohexyl methane at the conversion of 98-99.99%;
    2) When the conversion in step 1) is 90-98%, the feed is switched from 4,4'-diamino-diphenyl methane to a mixture of 2,4'-diamino-diphenyl methane and 4,4'-diamino-diphenyl methane, and the hydrogenation reaction is continued to prepare 2,4'-diamino-dicyclohexyl methane and 4,4'-diamino-dicyclohexyl methane;
    3) After the conversion of the mixture of 2,4'-diamino-diphenyl methane and 4,4'-diamino-diphenyl methane in step 2) is ≥90% and the reaction is lasted at said conversion for 20-40 h, the feed is switched from the mixture of 2,4'-diamino-diphenyl methane and 4,4'-diamino-diphenyl methane to 4,4'-diamino-diphenyl methane, and the hydrogenation reaction is continued to prepare 4,4'-diamino-dicyclohexyl methane.

2. The continuous method as claimed in claim 1, wherein the 4,4'-diamino-diphenyl methane feed is composed of 98-100 wt % 4,4'-diamino-diphenyl methane, 0-2 wt % 2,4'-diamino-diphenyl methane, 0-1 wt % N-methyl-4,4'-diamino diphenyl methane, and 0-1 wt % other impurities, based on the total weight of the 4,4'-diamino-diphenyl methane feed.

3. The continuous method as claimed in claim 1, wherein the mixture of 2,4'-diamino-diphenyl methane and 4,4'-diamino-diphenyl methane is composed of 83-95 wt % 4,4'-diamino-diphenyl methane, 3-16 wt % 2,4'-diamino-diphenyl methane, 0-1 wt % N-methyl-4,4'-diamino-diphenyl methane, and 0-1 wt % other impurities, based on the total weight of the mixture.

4. The continuous method as claimed in claim 1, wherein said catalyst is a supported metal catalyst, wherein the metal is one or more selected from Group VIIIB metals, the support is one or more selected from rare earth, diatomaceous earth, alumina, activated carbon, lithium aluminate, spinel, titania, silica and silica-alumina oxides, and the weight ratio of the metal and the support is 1-10:100.

5. The continuous method as claimed in claim 1, wherein said catalyst is a mixture of Rh/$Al_2O_3$ and Ru/$Al_2O_3$, wherein the weight ratio of Rh/Ru is 1-50:1.

6. The continuous method as claimed in claim 5, wherein the amount of Rh/$Al_2O_3$ is 0.5-5 wt %, based on the total weight of the reaction solution in the reaction tank.

7. The continuous method as claimed in claim 1, wherein the 4,4'-MDA feed is supplied in the presence of or in the absence of a solvent, and the concentration of 4,4'-MDA in the solution is 40-60 wt %.

8. The continuous method as claimed in claim 1, wherein the mixture of 2,4'-MDA and 4,4'-MDA is supplied in the presence of or in the absence of a solvent, and the total concentration of 2,4'-MDA and 4,4'-MDA in the solution is 40-60 wt %.

9. The continuous method as claimed in claim 7, wherein said solvent comprises one or more selected from cyclohexane, dioxane, tetrahydrofuran, cyclohexylamine, dicyclohexylamine, methanol, ethanol, isopropanol, n-butanol, 2-butanol and methyl cyclohexane.

10. The continuous method as claimed in claim 1, wherein the productivity of the catalyst for 4,4'-diamino-diphenyl methane in the step 1) is 0.4-1 g MDA/g cat/min, and the productivity of the catalyst for the mixture of 2,4'-diamino-diphenyl methane and 4,4'-diamino-diphenyl methane in the step 2) is 0.4-1 g MDA/g cat/min; and the reaction temperature of hydrogenation is 100-190° C., and the absolute reaction pressure is 5-15 MPa.

11. The continuous method as claimed in claim 2, wherein the 4,4'-diamino-diphenyl methane feed is composed of 99-100wt% 4,4'-diamino-diphenyl methane, 0-1wt% 2,4'-diamino-diphenyl methane, 0-0.5wt% N-methyl-4,4'-diamino-diphenyl methane, and 0-0.5wt% other impurities, based on the total weight of the 4,4'-diamino-diphenyl methane feed.

12. The continuous method as claimed in claim 3, wherein the 4,4'-diamino-diphenyl methane feed is composed of 85-95wt% 4,4'-diamino-diphenyl methane, 5-15wt% 2,4'-diamino-diphenyl methane, 0-0.5wt% N-methyl-4,4'-diamino-diphenyl methane, and 0-0.5wt% other impurities, based on the total weight of the mixture.

13. The continuous method as claimed in claim 4, wherein the metal is one or more selected from Pt, Rh, Ru, Ir and Pd.

14. The continuous method as claimed in claim 5, wherein the weight ratio of Rh/Ru is 30-40:1, wherein the content of Rh is 3-7wt%; and the contend of Ru is 3-7wt%.

15. The continuous method as claimed in claim 14, wherein the content of Rh is 4-6wt%, and the contend of Ru is 4-6wt%.

16. The continuous method as claimed in claim 6, wherein the amount of $Rh/Al_2O_3$ is 1-3wt%.

17. The continuous method as claimed in claim 7, wherein the 4,4'-MDA feed is supplied in the presence a solvent, and the concentration of 4,4'-MDA in the solution is about 50wt%.

18. The continuous method as claimed in claim 8, wherein the mixture of 2,4'-MDA and 4,4'-MDA is supplied in the presence of a solvent, and the total concentration of 2,4'-MDA and 4,4'-MDA in the solution is about 50wt%.

19. The continuous method as claimed in claim 9, wherein said solvent is tetrahydrofuran.

* * * * *